(12) United States Patent
Cai

(10) Patent No.: US 12,716,532 B2
(45) Date of Patent: Aug. 25, 2026

(54) FLUID HUB ASSEMBLY

(71) Applicant: CareFusion 303, Inc., San Diego, CA (US)

(72) Inventor: Frank Cai, Ontario, CA (US)

(73) Assignee: CAREFUSION 303, INC., San Diego, CA (US)

( * ) Notice: Subject to any disclaimer, the term of this patent is extended or adjusted under 35 U.S.C. 154(b) by 92 days.

(21) Appl. No.: 18/661,243

(22) Filed: May 10, 2024

(65) Prior Publication Data

US 2025/0347372 A1 Nov. 13, 2025

(51) Int. Cl.

*F16L 37/138* (2006.01)
*A61M 39/10* (2006.01)
*F16L 33/34* (2006.01)

(52) U.S. Cl.

CPC .......... *F16L 33/34* (2013.01); *A61M 39/1011* (2013.01); *A61M 2039/1027* (2013.01); *A61M 2207/00* (2013.01)

(58) Field of Classification Search

CPC . F16L 33/34; F16L 13/02; F16L 13/10; F16L 13/103; F16L 37/08123; F16L 37/138; F16L 47/02; F16L 2201/20; F16L 2201/40; F16L 2201/44; F16L 37/08; F16L 37/123; A61M 39/1011

See application file for complete search history.

(56) References Cited

U.S. PATENT DOCUMENTS 5,713,856 A 2/1998 Eggers et al.
6,874,522 B2 4/2005 Anderson et al.
7,004,934 B2 2/2006 Vaillancourt
7,040,598 B2 5/2006 Raybuck
7,153,296 B2 12/2006 Mitchell
7,350,764 B2 4/2008 Raybuck
7,396,051 B2 7/2008 Baldwin et al.
7,763,013 B2 7/2010 Baldwin et al.
7,766,394 B2 8/2010 Sage et al.
7,794,675 B2 9/2010 Lynn
7,803,139 B2 9/2010 Fangrow, Jr.

(Continued)

FOREIGN PATENT DOCUMENTS

EP 1678070 A2 7/2006
EP 1049514 B1 8/2006

(Continued)

OTHER PUBLICATIONS

International Search Report and Written Opinion for Application No. PCT/US2025/024059, dated Jul. 3, 2025, 18 pages.

(Continued)

*Primary Examiner* — Aaron M Dunwoody

(74) *Attorney, Agent, or Firm* — MASCHOFF BRENNAN

(57) ABSTRACT

A fluid connector assembly can be provided that permits ease of connection, secure connection with a fluid connector, and a safety release mechanism that enables the fluid connector assembly to safely disengage from the fluid connector. The fluid connector assembly can include a post and a hub that is slidably coupled to the post. When disconnected from the fluid connector, the hub can be locked or fixed at a lockout position, which can tend to prevent reconnection or reuse of the hub, thereby facilitating safe and sanitary medical practices.

13 Claims, 4 Drawing Sheets

(56) References Cited

U.S. PATENT DOCUMENTS 7,803,140 B2 9/2010 Fangrow, Jr.
7,815,614 B2 10/2010 Fangrow, Jr.
7,918,243 B2 4/2011 Diodati et al.
7,998,134 B2 8/2011 Fangrow et al.
8,123,738 B2 2/2012 Vaillancourt
8,142,418 B2 3/2012 Mcmichael et al.
8,211,069 B2 7/2012 Fangrow, Jr.
8,262,628 B2 9/2012 Fangrow, Jr.
8,361,408 B2 1/2013 Lynn
8,480,968 B2 7/2013 Lynn
8,777,908 B2 7/2014 Fangrow, Jr.
8,777,909 B2 7/2014 Fangrow, Jr.
8,795,256 B1 8/2014 Smith
8,888,758 B2 11/2014 Mansour
8,899,267 B2 12/2014 Diodati et al.
8,910,919 B2 12/2014 Bonnal et al.
8,974,425 B2 3/2015 Tachizaki et al.
8,974,437 B2 3/2015 Williams et al.
9,114,242 B2 8/2015 Fangrow et al.
9,126,028 B2 9/2015 Fangrow et al.
9,126,029 B2 9/2015 Fangrow et al.
9,192,753 B2 11/2015 Lopez et al.
9,234,616 B2 1/2016 Carrez et al.
9,358,379 B2 6/2016 Fangrow, Jr.
9,433,769 B2 9/2016 Bayly
9,468,749 B2 10/2016 Mansour et al.
9,492,649 B2 11/2016 Carrez et al.
9,636,492 B2 5/2017 Fangrow, Jr.
9,724,504 B2 8/2017 Fangrow, Jr. et al.
9,724,505 B2 8/2017 Williams et al.
9,861,805 B2 1/2018 Dennis et al.
9,933,094 B2 4/2018 Fangrow
9,974,939 B2 5/2018 Fangrow, Jr.
9,974,940 B2 5/2018 Fangrow, Jr.
10,029,086 B2 7/2018 Nowak et al.
10,156,306 B2 12/2018 Fangrow
10,173,045 B2 1/2019 Mansour
10,179,203 B1 1/2019 Huslage et al.
10,315,025 B2 6/2019 Phillips et al.
10,398,887 B2 9/2019 Fangrow, Jr. et al.
10,441,507 B2 10/2019 Sanders
10,518,078 B2 12/2019 Stjernberg Bejhed et al.
10,569,073 B2 2/2020 Hallisey et al.
10,625,068 B2 4/2020 Leuthardt et al.
10,655,768 B2 5/2020 Jones et al.
10,697,570 B2 6/2020 Fangrow
10,744,315 B2 8/2020 Sanders
10,842,982 B2 11/2020 Fangrow, Jr.
10,857,346 B2 12/2020 Dennis et al.
10,864,362 B2 12/2020 Jones et al.
10,881,847 B2 1/2021 Lynn
11,168,818 B2 11/2021 Fangrow
11,207,514 B2 12/2021 Kakinoki
11,235,135 B2 2/2022 Tsai
11,273,297 B2 3/2022 Kakinoki
11,484,471 B2 11/2022 Sanders
11,491,084 B2 11/2022 Ueda et al.
2004/0215158 A1 10/2004 Anderson
2005/0090805 A1 4/2005 Shaw et al.
2006/0129109 A1 6/2006 Shaw et al.
2007/0088292 A1 4/2007 Fangrow, Jr.
2007/0088293 A1 4/2007 Fangrow, Jr.
2007/0088294 A1 4/2007 Fangrow, Jr.
2007/0225635 A1 9/2007 Lynn
2008/0039803 A1 2/2008 Lynn
2011/0106046 A1 5/2011 Hiranuma
2014/0249487 A1 9/2014 Lynn
2014/0330254 A1 11/2014 Rosenberger et al.
2016/0000363 A1 1/2016 Jones et al.
2018/0200147 A1 7/2018 Sanders
2019/0184152 A1 6/2019 Kakinoki
2019/0282797 A1 9/2019 Tsai
2019/0285216 A1* 9/2019 Lo ......................... F16L 33/224
2020/0113784 A1 4/2020 Lopez et al.
2020/0179672 A1 6/2020 Kakinoki
2020/0215319 A1 7/2020 Fangrow, Jr. et al.
2020/0284385 A1 9/2020 Fangrow
2020/0323734 A1 10/2020 Ueda et al.
2020/0338331 A1 10/2020 Sanders
2021/0069484 A1 3/2021 Tsai
2021/0077803 A1 3/2021 Lynn
2021/0252267 A1 8/2021 Fangrow, Jr.
2021/0388926 A1 12/2021 Martin et al.
2021/0393938 A1 12/2021 Lynn et al.
2022/0260189 A1 8/2022 Deuse
2022/0282814 A1 9/2022 Fangrow
2022/0339423 A1 10/2022 Weber et al.

FOREIGN PATENT DOCUMENTS

EP 1517723 B1 1/2007
EP 1622675 B1 8/2009
EP 2144634 A1 1/2010
EP 2298407 A1 3/2011
EP 2694132 A1 2/2014
EP 2562456 B1 6/2014
EP 2782633 A1 10/2014
EP 1842002 B1 4/2015
EP 2736582 B1 5/2015
EP 2089094 B1 1/2016
EP 2219721 B1 12/2017
EP 2753396 B1 12/2017
EP 2736584 B1 4/2018
EP 3305361 A1 4/2018
EP 2271398 B1 11/2018
EP 2480281 B1 11/2018
EP 2790750 B1 11/2018
EP 2331191 B1 3/2019
EP 3079756 B1 3/2019
EP 2121114 B1 5/2019
EP 2719419 B1 5/2019
EP 3421077 B1 8/2019
EP 3570807 A1 11/2019
EP 3570809 A1 11/2019
EP 2536463 B1 4/2020
EP 3381505 B1 5/2020
EP 3538201 B1 5/2020
EP 1904152 B1 12/2020
EP 2150307 B1 12/2020
EP 3313490 B1 1/2021
EP 3760275 A1 1/2021
EP 3851155 A1 7/2021
EP 3517164 B1 9/2021
EP 3954355 A1 2/2022
EP 3960229 A1 3/2022
EP 3973044 A1 3/2022
EP 3305361 B1 5/2022
EP 3134052 B1 8/2022
EP 3530313 B1 8/2022
WO 9614096 A2 5/1996
WO WO-2021099437 A1 5/2021
WO WO-2021180675 A1 9/2021
WO WO-2021252197 A1 12/2021
WO WO-2022042956 A1 3/2022
WO WO-2022149339 A1 7/2022
WO WO-2022207560 A1 10/2022

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.

Icumedical, "ChemoClave™ Needlefree Close System Transfer Device (CSTD)", date unknown, https://www.icumed.com/products/oncology/closed-system-transfer-devices/chemoclave.

Icumedical, "ChemoLock™ Needlefree Closed System Transfer Device (CSTD)", date unknown, https://www.icumed.com/products/oncology/closed-system-transfer-devices/chemolock.

Ivteam, "Force-activated separation IV connectors", 2022, Retrieved from the internet https://www.ivteam.com/intravenous-literature/

(56) References Cited

OTHER PUBLICATIONS force-activated-separation-iv-connectors/ [Last retrieved Jan. 13, 2023].

Lineus Medical, SafeBreak Product Features and Benefits Brochure, May 2021, mkg 0058 5/21 Rev. 02.

PRZen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

Tribology, "Coefficient of friction, Rolling resistance and Aerodynamics", date unknown, https://www.tribology-abc.com/abc/cof.htm.

* cited by examiner

FLUID HUB ASSEMBLY

TECHNICAL FIELD

The present disclosure relates generally to medical fluid connectors and, more particularly, to a fluid hub assembly that includes medical connectors that are configured to connect and disconnect based on a certain threshold of force.

BACKGROUND

Peripheral intravenous ("PIVC") catheters are medical tools inserted into peripheral veins of patients to deliver medical fluid to the patients. In an example application, the medical fluid is delivered to the patient, and a medical professional subsequently removes the PIVC catheter from the patient. Often, however, these catheters are unintentionally dislodged. For example, catheter lines receiving an unintended or unexpected pulling force can pull the IV tubing, which pulls the catheter out of the patient. In other instances, catheters are accidentally removed from patients and medical professionals. Unintended or unexpected dislodgement can lead to patient blood loss, IV fluid loss, and IV fluid delivery delay.

Intravenous ("IV") connectors are specialized components used in medical devices and equipment for the secure and safe connection and disconnection of intravenous tubing. The design of these connectors typically includes a locking mechanism that allows the intravenous tubing to be interconnected so that a patient may be administered medications, nutrition, or other fluids based on their medical condition and treatment plan.

SUMMARY

In accordance with at least some embodiments disclosed herein is the realization that unintended dislodgement or disconnection of a medical connection, such as a medical fluid line, can result in injury to a patient or a medical professional, such as by depriving the patient of a medicament, increasing the potential for infection to the patient, and exposing the medical professional to medicaments.

Aspects of the present disclosure provide fluid connector assemblies with medical connectors, each of which include one or more fluid paths, that are configured to engage and disengage with tubing or other connectors based on a predetermined threshold of force. The connectors can be activated or released when a specific force is applied during the connection or disconnection process. This threshold of force can be calibrated to provide a secure connection during use while also facilitating manual disconnection by healthcare professionals or in other situations where an emergency disconnection is needed based on application of a sufficient force, so as to minimize patient trauma in the event of a fall, stretching of IV tubing, or other necessary disconnection event.

Aspects of the present disclosure also provide for a fluid hub assembly that can prevent reconnection therewith after the hub assembly has been disconnected from a tubing connector. For example, in some embodiments, the hub assembly can have a first, pre-assembly configuration in which the hub assembly can be coupled to a connector, a connected or assembled configuration which the assembly is coupled to the connector, and a second, disconnected configuration in which the hub assembly is separated from the connector. According to some aspects of the present disclosure, the first configuration can be different from the second configuration.

For example, one or more components of the hub assembly can be shifted to a locked position during this engagement with a connector, thereby preventing reconnection of the connector with the hub assembly.

According to certain embodiments, a fluid hub assembly can include a post and a hub that is configured to fit onto the post and connect with a tubing connector. The post can be a single, continuous part or be configured as to components that are coupled together with the hub. The post can comprise one or more motion-limiting structures that can engage with one or more components of the hub in order to restrict one or more degrees of motion of the hub relative to the post. For example, the motion limiting structures can comprise tabs, protrusions, and/or recesses, and the like, that can restrict longitudinal and/or rotational movement of the hub relative to the post.

In some embodiments, the hub can move between a ready or engaged position in which the hub is configured to be coupled with the fluid connector and a disengaged position in which the hub can release the fluid connector. Upon release of the fluid connector, the hub can be engaged with one or more lockout features of the post, which can prevent the hub from moving back towards a ready or engaged position. Therefore, in a locked-out or final fixation position the fluid hub assembly can prevent reconnection between the hub and the fluid connector.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present disclosure includes various features and advantages of a fluid hub assembly with medical connectors that are configured to connect and disconnect based on a certain threshold of force.

Figure 1:
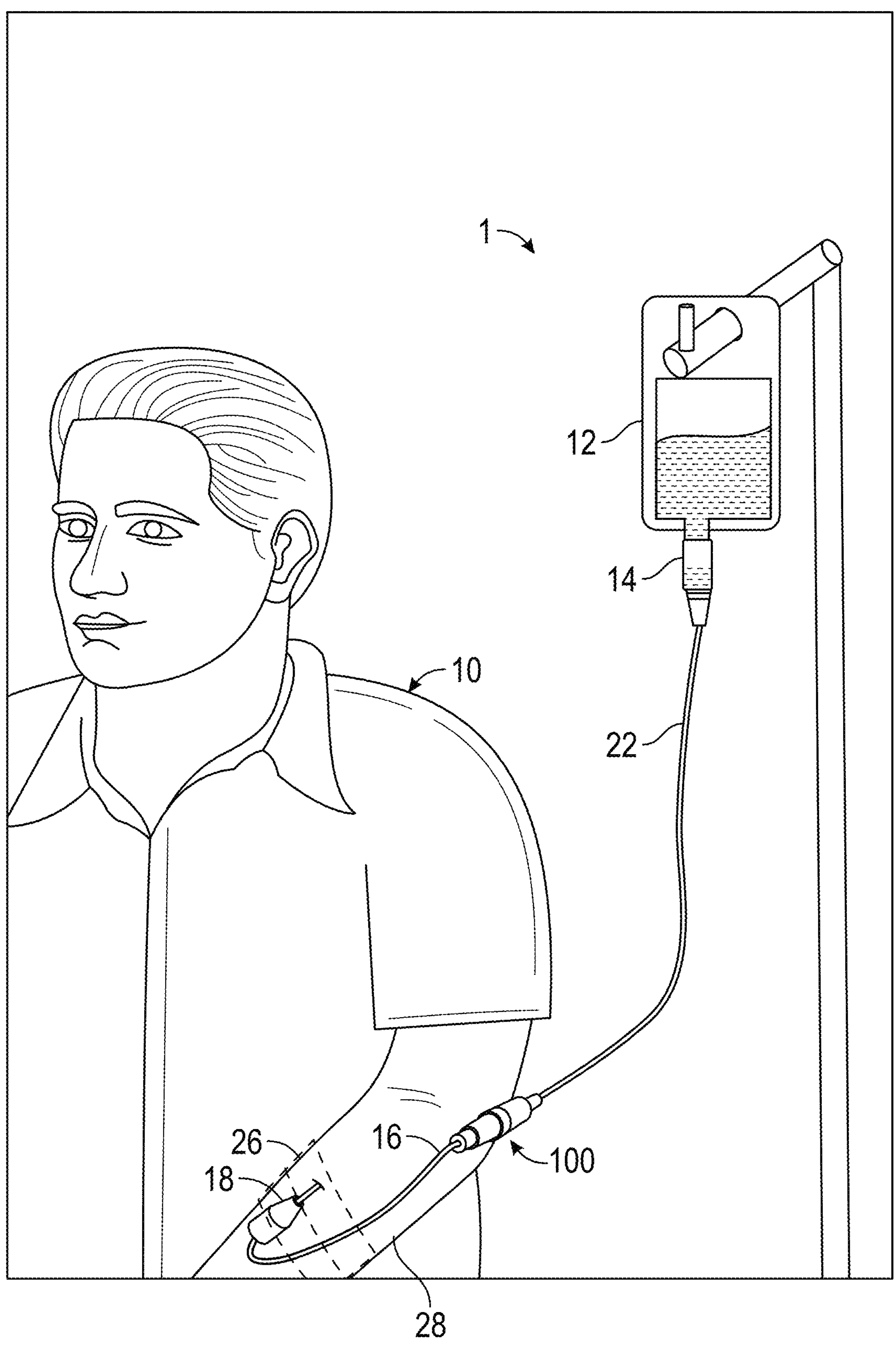
FIG. 1 illustrates an IV set coupled to a patient, in accordance with aspects of the present disclosure.

Referring now to the figures, FIG. 1 illustrates an IV set 1 coupled to an arm 28 of a patient 10, in accordance with some embodiments. The IV set 1 includes a medicament bag 12, a drip chamber 14, and tubing 22. The tubing 22 extends between the drip chamber 14 and a fluid hub assembly 100 of the IV set 1. To resist unintended dislodgement or disconnection of the tubing 16 or the catheter 18 from the patient, tape 26 is placed over the tubing 16 and the catheter 18, so that the tape 26 engages the tubing 16, the catheter 18, and the patient 10.

Figures 2A, 2B:
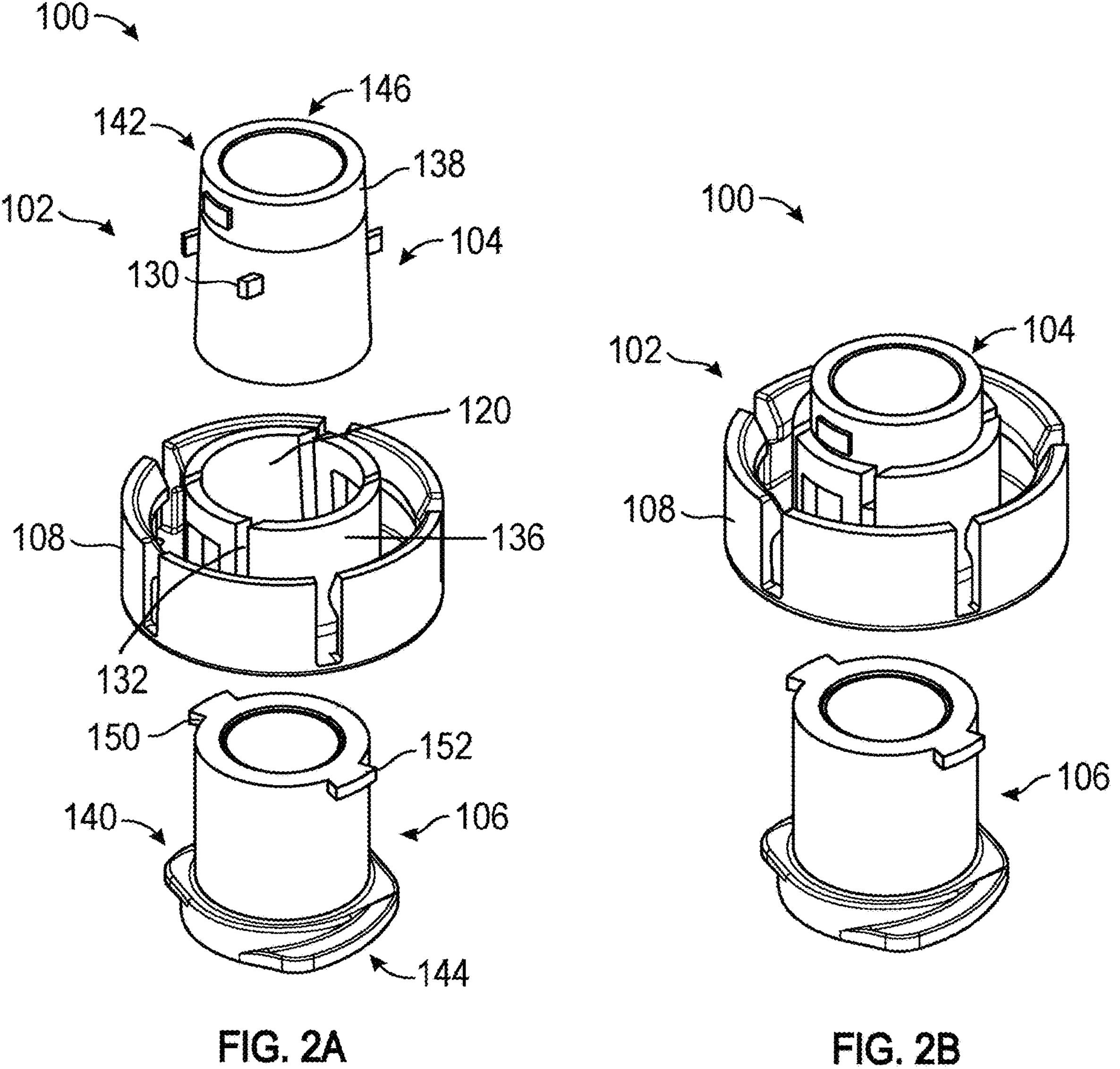
FIG. 2A illustrates an exploded perspective view of a fluid hub assembly, in accordance with some embodiments.
FIG. 2B illustrates a perspective view of the fluid hub assembly of FIG. 2, in a partially assembled configuration, in accordance with some embodiments.

FIGS. 2A and 2B illustrate a perspective view of a fluid hub assembly 100, in accordance with some embodiments. The fluid hub assembly 100 is designed for use in medical applications, such as the IV set 1 (shown in FIG. 1) as well as other IV medical fluid delivery applications using catheters, including PIVC catheters, as non-limiting examples.

The fluid hub assembly 100 can include a post and a hub coupled to the post. The post can comprise one or more engagement features that extend radially therefrom to permit engagement between the post and the hub, which can be slidably positioned over the post. The hub can be used to facilitate interconnection with tubing of the IV set, and as disclosed further herein, resist accidental disconnection of the tubing and facilitate quick reconnection and/or replacement of the IV connection components.

For example, as illustrated in FIGS. 2A and 2B, a hub 108 can comprise a central bore 120 through which a post 102 can extend. The post 102 can comprise one or more guide mechanisms 130, such as radially extending tabs or protrusions, that are configured to engage with a respective alignment mechanism 132 of the hub 108. When the post 102 is positioned within the bore 120 of the hub 108, the guide mechanism 130 can be slidingly engaged with the alignment mechanism 132 in order to restrict rotational movement of the hub 108 relative to the post 102, which is shown in FIG. 2B.

As shown in FIG. 2A, the guide mechanism 130 can comprise a plurality of radially extending tabs that extend from an outer surface of the post 102. For example, the guide mechanism 130 can comprise one, two, three, four, five, or six radially extending tabs. These tabs can be positioned within a common plane that extends perpendicular relative to a longitudinal axis of the post 102. The tabs also be circumferentially positioned about the outer surface of the post 102 in a symmetrical arrangement. For example, the tabs can each be positioned at approximately 90° away from each other such that four tabs are spaced substantially circumferentially equidistant from each other about the outer surface of the post 102. Further, as illustrated in FIG. 2A, the tabs can be positioned in two sets that not substantially circumferentially equidistant about the outer surface of the post 102, but are symmetrical about the longitudinal plane that extends through a longitudinal axis of the hub 108. Such an arrangement can advantageously facilitate rotational alignment of the post 102 relative to the hub 108 in order to align other features of the post 102 and the hub 108 relative to each other.

As also illustrated in FIG. 2A, the alignment mechanism 132 of the hub 108 can comprise one or more slots that extend longitudinally along a core component 136 of the hub 108. In some embodiments, the alignment mechanism 132 of the hub 108 can comprise one, two, three, four, five, or six slots. The slots can be configured to receive a respective tab of the guide mechanism 130 of the post 102. In accordance with some embodiments, the guide mechanism 130 can comprise four tabs and the alignment mechanism 132 can comprise more slots, thereby providing a robust anti-rotation mechanism that restricts relative rotational movement between the post 102 and the hub 108.

In order to reduce the likelihood that the guide mechanism 130 and/or the alignment mechanism 132 break or otherwise become damaged during assembly or use, the shape and dimensions of these features can be made more robust, according to some embodiments. For example, the tabs of the guide mechanism 130, if made too small, may be prone to breaking off during assembly. However, by adjusting the height (longitudinal extent, along the longitudinal axis of the post 102) of the tabs to provide a cross-section having a height-to-width ratio of at least 2:1, at least 3:1, at least 4:1, or greater, the rigidity and durability of the tab can be greatly increased. Further, adjusting the ratio of the depth/length of the tabs (how much the tabs extend away from the outer surface of the post 102) relative to the height of the tabs, to provide a height-to-depth ratio of at least 1:1, at least 2:1, at least 3:1, at least 4:1, or greater, can also greatly increase the rigidity and durability of the tab.

Moreover, some embodiments can be configured such that the guide mechanism 130 and the alignment mechanism 132 can be switched or adjusted between the post 102 and the hub 108. As generally illustrated in the figures and discussed in some embodiments above, the guide mechanism 130 has been shown as one or more protruding members, and the alignment mechanism 132 has been shown as one or more recesses configured to engage with the guide mechanism 130. This male and female relationship between the guide mechanism 130 and the alignment mechanism 132 can be switched so that the post 102 and the hub 108 each have one or more recesses or protrusions that can engage with a respective recess or protrusion of the other one of the post 102 or the hub 108.

For example, the post 102 can comprise at least one recess or slot along the outer surface thereof and the hub 108 can have at least one protrusion that can engage with the recess or slot of the outer surface of the post 102. Further, in some embodiments, the post 102 and the hub 108 can each comprise at least one recess or slot and at least one protrusion, and the alignment of these components can be facilitated by the circumferential positioning of the recess(es) and protrusion(s) thereof.

In some embodiments, the core component 136 of the hub 108 can define the central bore 120 of the hub 108 and be configured to have an inner dimension or diameter that permits the bore 120 to fit closely against the outer surface of the post 102. In some embodiments, the outer surface of the post 102 can have a tapering diameter that decreases from a thread engagement section 140 toward a distal section 142 thereof. Similarly, the bore 120 of the hub 108 can comprise a diameter that decreases corresponding to the decreasing diameter of the outer surface of the post 102.

As illustrated in FIGS. 2A and 2B, some embodiments can be configured such that the post 102 can be formed from two or more separate components that can be coupled, fused, or otherwise attached to each other and thereafter assembled with the hub 108. For example, the post 102 can comprise two components: a first post component 104 and a second post component 106 coupled with the first post component 104.

The first post component 104 and the second post component 106 may be referred to as a first connector and a second connector, respectively. However, "first" and "second" may be interchangeable. Also, each of the first and second components 104, 106 may be referred to as medical connectors. When the components 104, 106 are connected to each other as shown in FIG. 3A, a fluid path for medical fluid is established by the fluid hub assembly 100.

In some embodiments, the first and second post components 104, 106 can be attached to each other using a variety of methods, such as application of adhesive, welding (e.g., ultrasonic welding), bonding, mechanical engagement, or other means that will securely fashion the first and second post components 104, 106 to each other and permit a fluid impermeable joint to be formed therebetween.

Although some embodiments can be formed using multiple components to create the post 102, the post 102 can also be formed as a single, continuous component having the various mechanisms disclosed herein that are functional and capable of engaging with the hub 108 and other components, as needed. For example, the post 102 could be molded as a single part and engaged with the hub 108 in a manner that permits full function and use of the assembly as intended. However, in order to disassemble or disengage the hub 108 from the post 102, the hub 108 could be configured to break away from the post 102.

Further, a plug 138 can be installed onto the distal section 142 or tip of the post 102, such as on the first post component 104, which can avoid additional welding and placement of a cap thereon. This feature is illustrated in FIG. 2A, where the plug 138 is coupled to the first post component 104. As discussed above with regard to the joint between the first post component 104 and the second post component 106, the plug 138 can be coupled to the first post component 104 in a manner that provides secure attachment and a fluid-impermeable joint therebetween.

In some embodiments, the second post component 106 can be connected to a medical fluid (not shown). Further, in some embodiments, the first post component 104 can be connected to a catheter line (not shown) to enable delivery of a medical fluid to a catheter. In this regard, the second post component 106 may include a fluid inlet 144 that acts as a fluid receiving location for the fluid hub assembly 100. Also, the first post component 104 may include a fluid outlet 146 that acts as a fluid transmission location for the fluid hub assembly 100.

To facilitate the connection to the medical fluid, the second post component 106 may include a luer. In some embodiments, the luer can be female luer designed to mate with a male connector that is connected to the medical fluid. Similarly, to facilitate the connection to the catheter line, the first post component 104 may include a luer or other component. In some embodiments, the luer 112 is male luer designed to mate with a female connector that is connected to the catheter line. Each of the luers may conform to standards established by the International Organization for Standards ("ISO") to improve patient safety, minimize medical fluid leakage, and reduce misconnection with other connection devices.

Referring again to FIGS. 2A and 2B, the hub 108 can be attached to the post 102 and the first and second post components 104, 106 can be joined together during the disassembly process. This assembly process can produce the fluid hub assembly 100, which is illustrated in FIG. 3A.

When assembled, the hub 108 can slide along or move longitudinally along the post 102 until contacting a stop member, which can limit longitudinal motion of the hub 108 along the post 102. For example, the stop member can comprise one or more shoulder members 150, 152 that extend radially from the outer surface of the post 102. As illustrated in FIGS. 2A and 2B, the shoulder members 150, 152 can form part of the second post component 106 and be longitudinally spaced apart from the guide mechanism 130. Thus, when assembled together, with the hub 108 positioned along the post 102, the hub 108 can move longitudinally until contacting the shoulder members 150, 152, which will restrict further longitudinal movement of the hub 108 in a direction toward the fluid inlet 144 of the post 102.

According to some embodiments, the post 102 can be fully assembled after the hub 108 is moved onto a lower section (opposite the fluid outlet 146) of the first post component 104. In other words, the first post component 104 can be slid into the central bore 120 of the hub 108 and thereafter, the first post component 104 can be joined to the second post component 106, as discussed above. The hub 108 will thereby be restricted from movement toward the fluid inlet 144, capable only of movement towards the fluid outlet 146. Moreover, the robust support provided by the shoulder members 150, 152 can allow the hub 108 to be supported by the post 102 in a shoulder-contacting or engaged position 162 against a downwardly exerted force (i.e., in the direction of the fluid inlet 144) applied during connection of tubing with the hub 108. For example, FIG. 3A illustrates the hub 108 in the shoulder-contacting or engaged position 162. While the hub 108 is connected with the tubing, the fluid seal between the tubing and the hub 108 and post 102 can be secure and the assembly can be used for fluid delivery.

Moreover, in accordance with some embodiments disclosed herein, the fluid hub assembly 100 can advantageously provide an accidental disconnection safety feature. For example, the fluid have assembly 100 can provide a medical connection, having one or more fluid paths, and be configured to engage and disengage with tubing or other connectors based on a predetermined threshold of force. The connectors can be activated or released when a specific force is applied during the connection or disconnection process. This threshold of force can be calibrated to provide a secure connection during use while also facilitating manual disconnection by healthcare professionals or in other situations where an emergency disconnection is needed based on application of a sufficient force, so as to minimize patient trauma in the event of a fall, stretching of IV tubing, or other necessary disconnection event.

In accordance with some embodiments, various advantages and benefits can be achieved implementing features of the fluid have assembly disclosed herein. For example, by requiring a specific force for connection and disconnection, these connectors help prevent accidental disconnections, which can lead to medication errors or compromise patient safety; however, upon application of sufficient force, the connection can be broken, thereby minimizing any patient trauma or discomfort. A consistent application of force ensures reliable connections, reducing the risk of leaks or air ingress into the IV line, which can affect medication delivery or patient care. Therefore, some embodiments disclosed herein can be configured with force threshold technology that can play a crucial role in enhancing the safety, reliability, and usability of intravenous administration systems in medical settings, ultimately contributing to improved patient outcomes and quality of care.

Figure 3B:
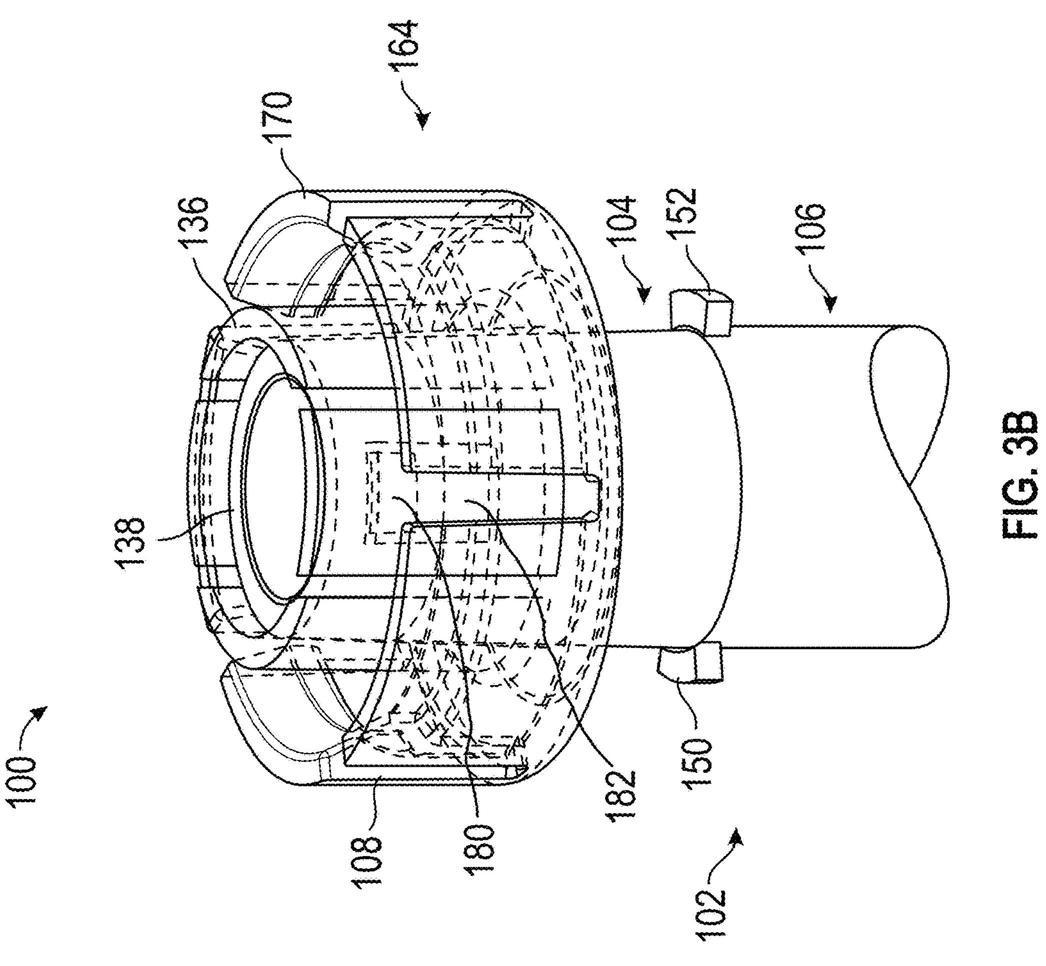
FIG. 3B illustrates a perspective view of the fluid hub assembly of FIG. 2, in an assembled, extended configuration, in accordance with some embodiments.
Figure 3A:
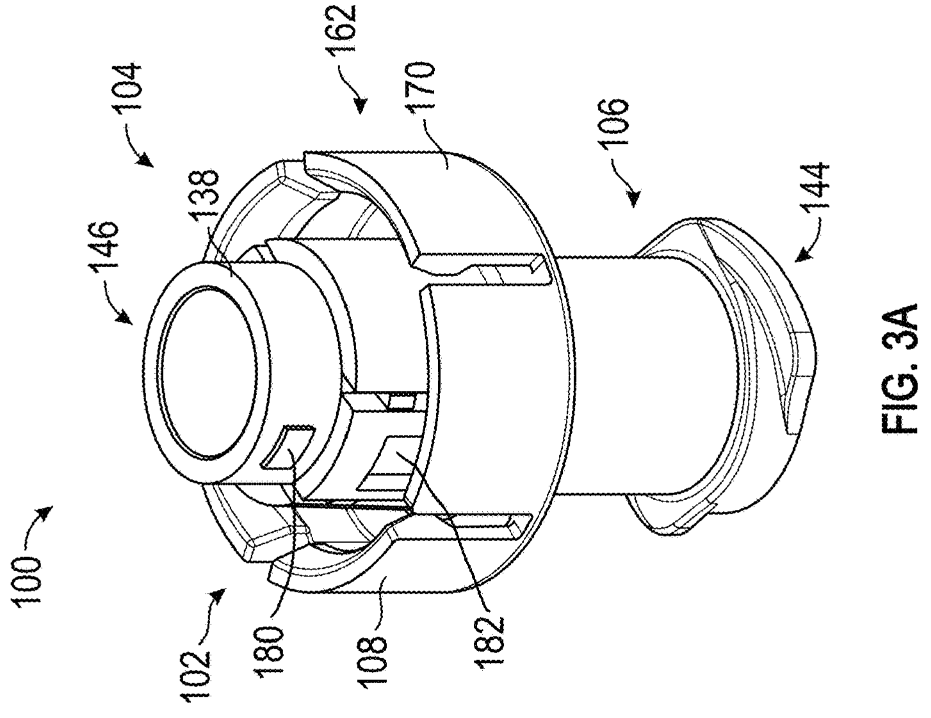
FIG. 3A illustrates a perspective view of the fluid hub assembly of FIG. 2, in an assembled configuration, in accordance with some embodiments.

For example, referring to FIG. 3B, the hub 108 can move from the engaged position 162 to a disengaged position 164, which may occur due to a disconnection event (e.g., an accidental force or pull applied to the tubing that creates a separating force on the fluid hub assembly 100). In response to such an event, the hub 108 can permit the tubing to be disengaged therefrom in order to mitigate any damage or trauma to the patient or other medical equipment.

As the hub 108 is moved toward the disengaged position 164, as shown in FIG. 3B, the hub 108 is moved upwardly toward the fluid outlet 146, away from the shoulder members 150, 152. As the separation force is applied to the hub 108, outer petals 170 of the hub 108 can radially deflect to permit disengagement of the tubing from the hub 108. The hub 108 can comprise a plurality of petals 170 that are separated by longitudinally extending slots. The embodiment illustrated provides five petals 170.

In accordance with some embodiments, as a disconnection event occurs, the hub 108 can be pulled to a location whereat the hub 108 extends or protrudes longitudinally beyond a top edge of the plug 138, as shown in FIG. 3B. For example, a top edge of the core component 136 can be pulled to extend longitudinally beyond the top edge of the plug 138. In this position, the hub 108 will be disengaged and achieve the disengaged position 164.

As the hub 108 is drawn or moves toward the disengaged position 164, a lockout mechanism can be engaged that restricts the hub 108 from moving back toward the engaged position 162 or back toward the shoulder members 150, 152. An occurrence of some embodiments, the lockout mechanism can comprise a combination of at least one slot and at least one protrusion that fits into the slot. The assembly 100 can be configured such that the hub 108 comprises the slot or the protrusion and the post 102 or plug 138 comprises the other one of the slot or the protrusion. For example, the embodiment illustrated in FIGS. 3A and 3B, the plug 138 comprises a radial protrusion 180 and the core component 136 of the hub 108 comprises a slot 182 that is configured to receive the protrusion 180 as the hub 108 moves towards the disengaged position 164. Once the protrusion 180 is received into the slot 182, the core component 136 can provide sufficient radial inward force that maintains engagement between the slot 182 and the protrusion 180 to restrict longitudinal movement of the hub 108 relative to the post 102 and the plug 138.

In accordance with some embodiments, the protrusion 180 can be configured as a ramp, wedge, or deflectable tab having a tapered configuration that has a blunt top end surface or profile that is largest nearer to the outlet and 146 than to the inlet end 144. In some embodiments, a deflectable tab can permit the core component 136 to push the deflectable tab toward or into the central bore 120 until the deflectable tab can rebound and snap into engagement with the slot 182. Regardless of the embodiment, the core component 136 can slide up the ramped surface of the protrusion 180 or deflectable tab until the core component 136 and the slot 182 snap down onto the protrusion 180 or deflectable tab to fix the protrusion 180 or deflectable tab within the slot 182. The blunt top end surface of the protrusion 180 or deflectable tab can abut an inner edge of the slot 182, thereby restricting movement of the core component 136 back toward the shoulder members 150, 152. Thus, the hub 108 can achieve a locked-out or final fixation position at which the hub 108 cannot be moved down toward the shoulder members 150, 152.

In accordance with some embodiments, the relative positions of the protrusion 180 (or deflectable tab) and the slot 182 can be modified in order to adjust a "snap length" between the post 102 and the hub 108. The length of relative motion between the hub 108 and the post 102 from the engaged position 162 to the disengaged position 164 can allow the assembly 100 to respond differently to disconnection events. For example, a shorter distance may provide a more immediate and responsive disconnection, while a longer distance may allow the assembly 100 to withstand a slightly greater disconnection event, including slightly greater disconnection forces.

Moreover, one of the advantages of locking out or fixing the hub 108 at the disengaged position 164 after a disconnection event is to ensure that the hub 108 cannot be reconnected to the tubing, thereby preventing reuse of potentially contaminated equipment. The final fixation position of the hub 108 at the disengaged position 164 can therefore signal to the clinician that the assembly 100 needs to be reconfigured, replaced, and/or cleaned before further fluid delivery can take place.

Figure 4D:
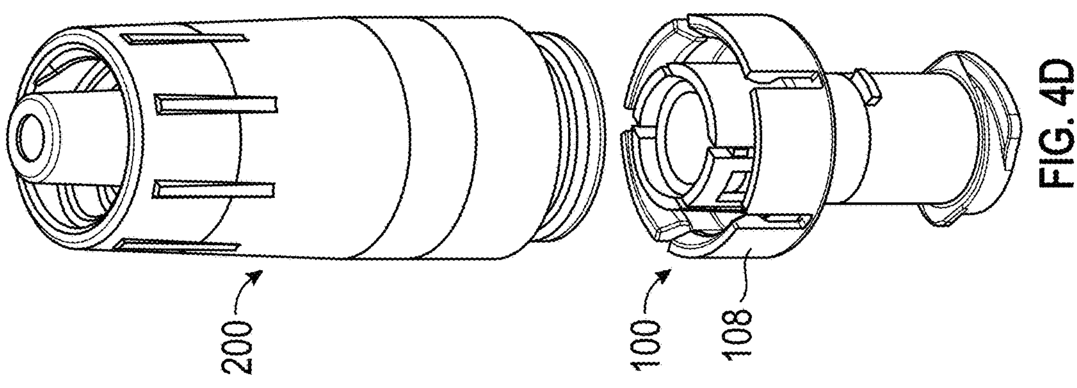
FIGS. 4A-4D illustrate views of the engagement and disengagement of the fluid hub assembly with a tubing connector, in accordance with some embodiments.
Figure 4C:
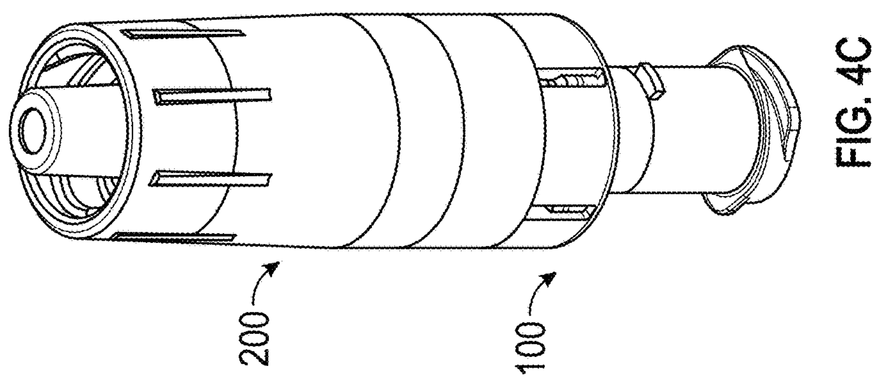
Figure 4B:
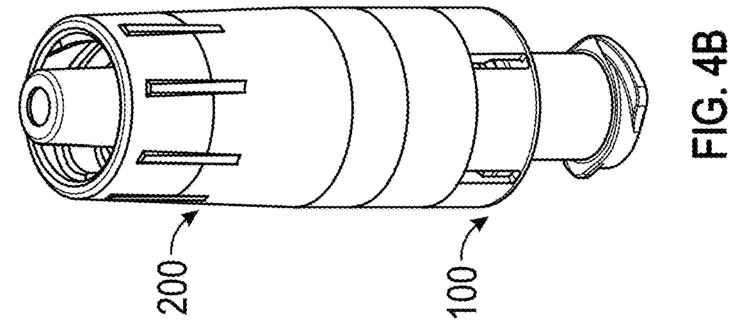
Figure 4A:
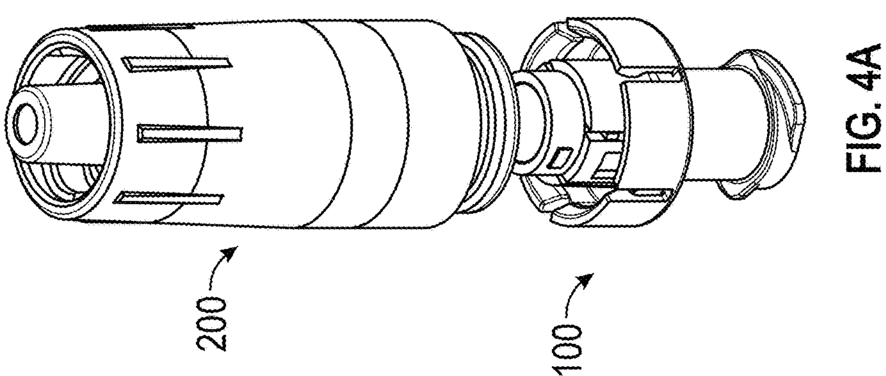

Referring to FIGS. 4A-4D, the connection and disconnection processes are illustrated, including the locked-out or final fixation position of the hub 108. As shown in FIG. 4A, the fluid hub assembly 100 can be assembled and positioned in the disengaged position. A tubing connector 200 can be moved into engagement with the fluid hub assembly 100, as shown in FIG. 4B. When engaged, the tubing connector 200 and the fluid hub assembly 100 can move as a collective unit, providing a sealed fluid pathway for delivery of fluids. However, as a disconnection event takes place, as shown in FIG. 4D, the tubing connector 200 can be separated from the fluid hub assembly 100, leaving the hub 108 in the final fixation position. Thereafter, the hub 108 can be removed and replaced with a new hub, or the entire assembly 100 can be removed from the luer connector and replaced with a new assembly.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 11, clause 17, clause, clause 23, clause 26, or clause 29. The other clauses can be presented in a similar manner.

Clause 1. A lock-out hub assembly, comprising: a two-part post having first and second post components, the first post component being connectable to the second post component at a post joint to form a continuous tubular member having a longitudinal axis, the first post component comprising a guide mechanism disposed along an exterior surface thereof, the second post component comprising a stopper mechanism disposed along an exterior surface thereof; and a hub comprising an engagement component and a central lumen that is alignable with the longitudinal axis of the tubular member and configured to permit the first post component to be positioned therethrough when the first and second post components are in a disconnected state, the hub further comprising an alignment mechanism for engaging with the guide mechanism of the first post component for restricting rotational movement of the hub relative to the first post component when the hub is coupled to the first post component, the hub being restricted from longitudinal movement relative to the second post component by the stopper mechanism of the second post component when the first and second post components are connected together in a joined state.

Clause 2. The hub assembly of clause 1, wherein the guide mechanism of the first post component comprises at least one arm extending from the exterior surface of the first post component.

Clause 3. The hub assembly of clause 2, wherein the alignment mechanism of the hub comprises a groove configured to receive the at least one arm of the first post component.

Clause 4. The hub assembly of clause 1, wherein the guide mechanism comprises four arms extending from the exterior surface of the post component.

Clause 5. The hub assembly of clause 4, wherein the four arms are positioned symmetrically about the exterior surface of the first post component.

Clause 6. The hub assembly of clause 5, wherein the alignment mechanism of the hub comprises four grooves that are each configured to receive a respective one of the four arms of the first post component.

Clause 7. The hub assembly of clause 1, wherein the first and second post components comprise a tapered tubular outer profile.

Clause 8. The hub assembly of clause 1, wherein the stopper mechanism of the second post component comprises a pair of stopper members extending from the exterior surface thereof.

Clause 9. The hub assembly of clause 8, wherein the pair of stopper members are disposed adjacent to the post joint.

Clause 10. The hub assembly of clause 1, wherein the post joint comprises a seam formed by opposing surfaces of the first and second post components whereat the first and second post components are joined together.

Clause 11. The hub assembly of clause 10, wherein the post joint comprises a section of material of the first and second post components that is fused together.

Clause 12. The hub assembly of clause 1, wherein the first post component comprises a post lockout mechanism, and wherein the hub comprises a hub lockout mechanism configured for engaging with post lockout mechanism to restrict longitudinal movement of the hub relative to the first post component.

Clause 13. The hub assembly of clause 12, wherein the post lockout mechanism comprises a deflectable tab configured to pivot in a direction transverse relative to the longitudinal axis.

Clause 14. The hub assembly of clause 13, wherein the hub lockout mechanism comprises an aperture that is accessible along an inner surface of the central lumen of the hub, the aperture being alignable with the deflectable tab of the post lockout mechanism for permitting the deflectable tab to move to an extended position, wherein the deflectable tab engages with the hub in the extended position for restricting longitudinal movement of the relative to the first component.

Clause 15. A lock-out hub assembly, comprising: a tubular post component having an exterior surface and comprising a longitudinal axis, a guide mechanism disposed along the exterior surface thereof, and a stopper mechanism disposed along the exterior surface; and a hub comprising an engagement component and a central lumen that is alignable with the longitudinal axis and configured to permit the tubular post component to be positioned therethrough, the hub further comprising an alignment mechanism for engaging with the guide mechanism of the tubular post component for restricting rotational movement of the hub relative to the tubular post component, wherein longitudinal movement of the hub relative to the tubular post component is restricted by engagement of the stopper mechanism against the hub.

Clause 16. The hub assembly of clause 15, wherein the guide mechanism of the tubular post component comprises at least one arm extending from the exterior surface.

Clause 17. The hub assembly of clause 16, wherein the alignment mechanism of the hub comprises a groove configured to receive the at least one arm of the tubular post component.

Clause 18. The hub assembly of clause 15, wherein the guide mechanism comprises four arms extending from the exterior surface of the post component.

Clause 19. The hub assembly of clause 18, wherein the four arms are positioned symmetrically about the exterior surface of the tubular post component.

Clause 20. The hub assembly of clause 19, wherein the alignment mechanism of the hub comprises four grooves that are each configured to receive a respective one of the four arms of the tubular post component.

Clause 21. The hub assembly of clause 15, wherein the tubular post component comprises a tapered tubular outer profile.

Clause 22. The hub assembly of clause 15, wherein the stopper mechanism of the tubular post component comprises a pair of stopper members extending from the exterior surface thereof.

Clause 23. The hub assembly of clause 22, wherein the pair of stopper members are disposed along a midsection of the tubular post component.

Clause 24. The hub assembly of clause 15, wherein the tubular post component comprises a post lockout mechanism, and wherein the hub comprises a hub lockout mechanism configured for engaging with post lockout mechanism to restrict longitudinal movement of the hub relative to the tubular post component.

Clause 25. The hub assembly of clause 24, wherein the post lockout mechanism comprises a deflectable tab configured to pivot in a direction transverse relative to the longitudinal axis.

Clause 26. The hub assembly of clause 25, wherein the hub lockout mechanism comprises an aperture that is accessible along an inner surface of the central lumen of the hub, the aperture being alignable with the deflectable tab of the post lockout mechanism for permitting the deflectable tab to move to an extended position, wherein the deflectable tab engages with the hub in the extended position for restricting longitudinal movement of the relative to the tubular post component.

Clause 27. A method of assembling a lock-out hub assembly, the method comprising: inserting a first post component into a central lumen of a hub; engaging a guide mechanism of the first post component with an alignment mechanism of the hub for restricting rotation of the hub relative to the first post component; and coupling a second post component to the first component to form a post joint, the second post component having a stopper mechanism configured to limit longitudinal movement of the hub along a longitudinal axis of the first and second post components.

Clause 28. The method of clause 27, wherein the engaging the guide mechanism comprises positioning an arm extending from an outer surface of the first post component within a groove of the hub.

Clause 29. The method of clause 27, wherein the engaging the guide mechanism comprises positioning two pairs of arms extending from the outer surface of the first post component withing respective grooves of the hub.

Clause 30. The method of clause 27, wherein the coupling comprises fusing the first post component to the second post component.

Clause 31. The method of clause 30, wherein the fusing comprises ultrasonic welding of opposing surfaces of the first post component and the second post component.

Clause 32. The method of clause 27, further comprising sliding the hub along a longitudinal axis of the first post component to engage a post lockout mechanism of the first post component with a hub lockout mechanism of the hub for restricting longitudinal movement of the hub relative to the first post component.

Clause 33. The method of clause 32, wherein the post lockout mechanism comprises a deflectable tab and the hub lockout mechanism comprises an aperture, and wherein the engagement of the post lockout mechanism with the hub lockout mechanism comprises permitting the deflectable tab to extend into the aperture of the hub.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A lock-out hub assembly, comprising:

a two-part post having first and second post components, the first post component being connectable to the second post component at a post joint to form a tubular member having a longitudinal axis, the first post component comprising a guide mechanism disposed along an exterior surface thereof, the second post component comprising a stopper mechanism disposed along an exterior surface thereof; and a hub comprising an engagement component and a central lumen that is alignable with the longitudinal axis of the tubular member and configured to permit the first post component to be positioned therethrough when the first and second post components are in a disconnected state, the hub further comprising an alignment mechanism for engaging with the guide mechanism of the first post component for restricting rotational movement of the hub relative to the first post component when the hub is coupled to the first post component, the hub being restricted from longitudinal movement relative to the second post component by the stopper mechanism of the second post component when the first and second post components are connected together in a joined state.

2. The hub assembly of claim 1, wherein the guide mechanism of the first post component comprises at least one tab extending from the exterior surface of the first post component.

3. The hub assembly of claim 1, wherein the guide mechanism comprises four tabs extending from the exterior surface of the post component.

4. The hub assembly of claim 1, wherein the first and second post components comprise a tapered tubular outer profile.

5. The hub assembly of claim 1, wherein the stopper mechanism of the second post component comprises a pair of stopper members extending from the exterior surface thereof.

6. The hub assembly of claim 1, wherein the post joint comprises a seam formed by opposing surfaces of the first and second post components whereat the first and second post components are joined together.

7. The hub assembly of claim 1, wherein the first post component comprises a post lockout mechanism, and wherein the hub comprises a hub lockout mechanism configured for engaging with post lockout mechanism to restrict longitudinal movement of the hub relative to the first post component.

8. A method of assembling a lock-out hub assembly, the method comprising:

inserting a first post component into a central lumen of a hub;

engaging a guide mechanism of the first post component with an alignment mechanism of the hub for restricting rotation of the hub relative to the first post component; and coupling a second post component to the first component to form a post joint, the second post component having a stopper mechanism configured to limit longitudinal movement of the hub along a longitudinal axis of the first and second post components.

9. The method of claim 8, wherein the engaging the guide mechanism comprises positioning a tab extending from an outer surface of the first post component within a groove of the hub.

10. The method of claim 8, wherein the engaging the guide mechanism comprises positioning two pairs of tabs extending from the outer surface of the first post component withing respective grooves of the hub.

11. The method of claim 8, wherein the coupling comprises fusing the first post component to the second post component.

12. The method of claim 11, wherein the fusing comprises ultrasonic welding of opposing surfaces of the first post component and the second post component.

13. The method of claim 8, further comprising sliding the hub along a longitudinal axis of the first post component to engage a post lockout mechanism of the first post component with a hub lockout mechanism of the hub for restricting longitudinal movement of the hub relative to the first post component.

* * * * *